United States Patent [19]

Lewis et al.

[11] 4,372,152

[45] Feb. 8, 1983

[54] BRINELL HARDNESS MEASURING SYSTEM

[75] Inventors: Edwin B. Lewis, Evington; Roy N. Moore, Jr., Concord, both of Va.

[73] Assignee: The Mead Corporation, Dayton, Ohio

[21] Appl. No.: 226,301

[22] Filed: Jan. 19, 1981

[51] Int. Cl.³ ..................... G01N 3/42; G01N 21/01
[52] U.S. Cl. ................................ 73/81; 356/378
[58] Field of Search ............... 73/81; 356/36, 378, 356/384; 209/599

[56] References Cited

U.S. PATENT DOCUMENTS 3,295,363  1/1967  Delporte ........................... 73/81
3,822,946  7/1974  Rynkowski ....................... 73/81

FOREIGN PATENT DOCUMENTS 358648  11/1972  U.S.S.R. ........................... 73/81

Primary Examiner—Herbert Goldstein
Attorney, Agent, or Firm—Charles N. Shane, Jr.

[57] ABSTRACT

This invention relates to a process for automatically measuring the Brinell Hardness of a casting for the purpose of creating data for use in making an accept-/reject decision. Process includes the steps of preparing a casting and positioning the casting on retention means positioned on a conveyor. A surface of the casting is selected for testing and this first surface is subjected to a first surface preparation step which consists of an abrasive grinding and/or machining to remove any irregularities in this surface. A second surface preparation step is then performed which comprises applying a contrast enhancing material to at least a portion of this preselected surface. Brinell Hardness testing apparatus is then used to test the casting for hardness and is then fed into appropriate means either human or mechanical for making an accept/reject decision as to the suitability of the casting for its intended use.

2 Claims, 1 Drawing Figure

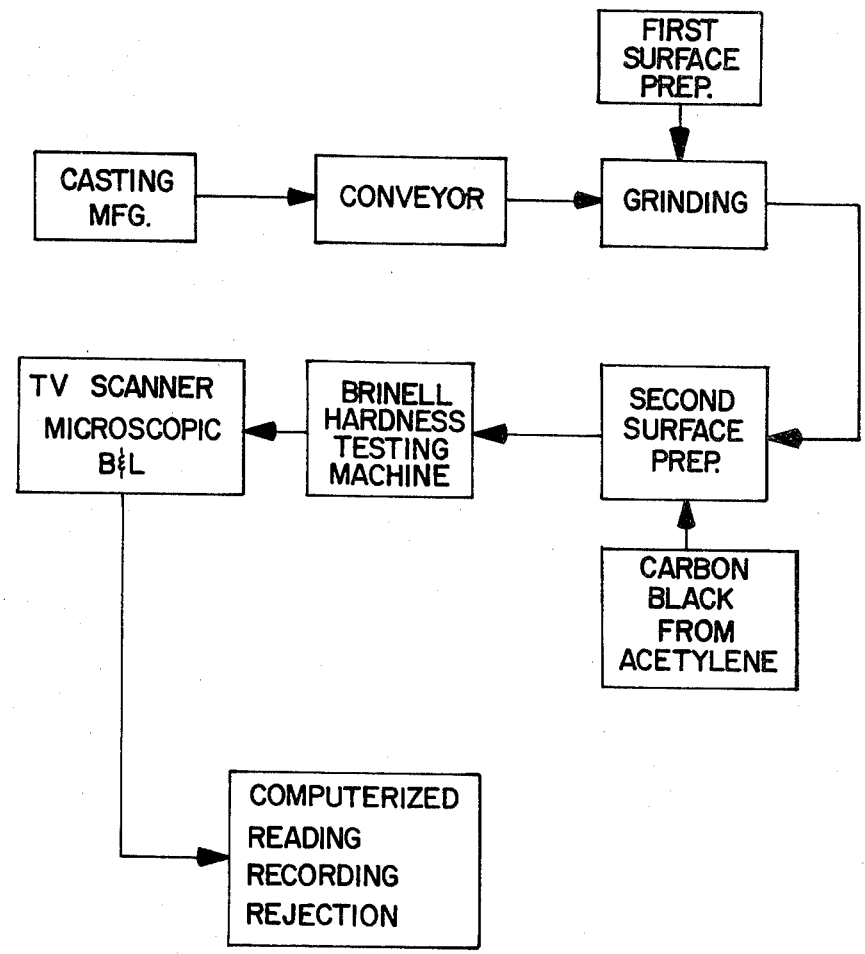

BRINELL HARDNESS MEASURING SYSTEM

BACKGROUND OF THE INVENTION

1. Field of the Invention

The present invention relates to a process for measuring the hardness of ductile iron castings using Brinell measuring apparatus. In particular, this invention relates to an automatic process for such hardness measurement whereby an accept/reject decision can be made automatically and accurately.

2. Prior Art

The Brinell Hardness test is an indentation hardness test using calibrated machines to force a hard ball, under specified conditions, into the surface of the material under test and to measure the diameter of the resulting impression after the removal of the load. From this measurement, a Brinell Hardness number is developed which is related to the applied load and to the surface area of the permanent impression made by a ball indenter computed from a mathematical equation. The mathematical equation, which is not important for purposes of this application, includes variables such as applied load, diameter of the ball and the mean diameter of the impression.

Historically, the Brinell method of hardness determination has been used for the purpose of verification or reference when a high degree of accuracy in metal castings is required, and alternately in some routine tests where somewhat lower degree of accuracy is permissible. There has, however, been a substantial amount of difficulty in using the Brinell Hardness system and apparatus where a high degree of accuracy is routinely required. As a specific example, an automobile casting, and especially those castings which are used in especially sensitive parts such as brake and steering systems, need to be tested constantly for hardness. Although the Brinell system is an established and known system for such measurements, it has not been possible in the past to automate such a hardness test to the point of routine use.

By practice of the process of this invention, it is possible to routinely use Brinell measurement apparatus to automatically measure the hardness of a metal casting and to create a permanent record with regard to hardness from which an appropriate accept/reject decision can be made as to the ultimate casting. The permanent record can also be retained for future verification of casting standards and specifications.

One of the areas of novelty in this invention is the surface preparation step which involves the use of what will be referred to hereinafter as a contrast enhancement material. The precise function of this material and the significance of this surface preparation step will become apparent after a further description of the Brinell reading system itself.

SUMMARY OF THE INVENTION

This invention relates to a process for automatically measuring the Brinell Hardness of a casting for the purpose of creating data for use in making an accept/reject decision. Process includes the steps of preparing a casting and positioning the casting on retention means positioned on a conveyor. A surface of the casting is selected for testing and this first surface is subjected to a first surface preparation step which consists of an abrasive grinding and/or machining to remove any irregularities in this surface. A second surface preparation step is then performed which comprises applying a contrast enhancing material to at least a portion of this pre-selected surface. Brinell Hardness testing apparatus is then used to test the casting for hardness and is then fed into appropriate means either human or mechanical for making an accept/reject decision as to the suitability of the casting for its intended use.

BRIEF DESCRIPTION OF THE DRAWING

FIG. 1 is a schematic of the system of the present invention.

DETAILED DESCRIPTION OF THE PREFERRED EMBODIMENT

For the purposes of promoting and understanding of the principles of the invention, reference will now be made to the embodiment illustrated in the drawing and specific language will be used to describe the same. It will nevertheless be understood that no limitation of the scope of the invention is thereby intended, such alterations and further modifications in the illustrated device, and such further applications of the principles of the invention as illustrated therein being contemplated, as would normally occur to one skilled in the art to which the invention relates.

Naturally, the first step in the process of this invention is the manufacture of a casting, preferably a ductile iron casting. In the preferred embodiment of this invention, this will involve the manufacture of a medium size automotive casting meant for use in an item such as a brake caliper, steering spindle or other cast part. However, the process of this invention is equally applicable to any operation involving the testing of metal castings for Brinell Hardness.

In the most preferred process of this invention, the casting is supported on a conveyor mechanism by a plurality of pins. This support structure enables the casting to be presented to the preparation and reading apparatus under precisely the same configuration each time so that the Brinell Hardness results which are obtained by use of this process are both accurate and reproducible. In the past, this has been a substantial problem in the testing of castings and the like on a routine basis as even the slightest misalignment of the metal casting will give different readings for purposes of comparison and for the meeting of appropriate standards.

The aligned casting is then conveyed to what is referred to as the first surface preparation step. In this step the finish of the portion of the casting which has been selected for hardness measurement is prepared. When necessary, the surface on which the Brinell impression is to be made is filed, ground, machined or polished with abrasive material so that the edge of the Brinell impression is clearly enough defined to permit accurate measurement of the diameter to the specified accuracy. The portion of the specimen to be tested must also be carefully selected such that no bulge or other marking showing the effect of the load appears on the side of the casting opposite the impression. In any event, the thickness of the casting at the place at which the Brinell impression is to be made should be at least ten times the depth of the proposed indentation.

After the first surface preparation step, the casting is conveyed to a second surface preparation step. At this second surface preparation step, the portion of the casting to be measured for hardness is prepared by applying what is referred to as a contrast enhancing material. As can be appreciated, the polished or ground surface of the casting is silvery-metallic in appearance. When the appropriate impression is made during the Brinell testing, the contrast between the leveled portion of the casting and the impression made by the Brinell ball is critical in determining the diameter of the impression which leads directly to the evaluation of the hardness. By applying a black or contrast enhancement material, the ability of even the human technician or machine to read the diameter of the impression is greatly enhanced.

This second surface enhancement step, which is critical in the process of this invention, is accomplished by the application of flat black paint, glass frosting, colloidal graphite, carbon black or mixtures of these with any of a variety of well known application apparatus. These materials can be applied by either mechanical or human means. Examples of appropriate application means would be a brush, pressurized spraying aparatus, an oxygen-low acetylene or other oxygen-low gas torch, both of which will apply an appropriate layer of carbon black.

After the contrast enhancement material has been added, the casting is conveyed to the Brinell measuring apparatus. In general, the Brinell measuring apparatus comprises a testing machine, Brinell balls and a measuring microscope.

The testing machine applies a pre-determined indenting load to a ball in contact with the casting. The magnitude of the indenting load is limited to certain discrete values. The design of the testing machine is generally such that no rocking or lateral movement of the indenter or the casting occurs while the load is being applied. In certain instances, machines employing a dead weight system are used in which case precautions are normally advised to prevent a momentary overload caused by the inertia of the dead weight system.

The standard test method for Brinell Hardness of metallic materials is generally described in the American National Standard ANSI/ASTM E 10-78. In this official document, specifications for Brinell balls are disclosed. The standard ball for Brinell Hardness testing is 10 mm in diameter with a deviation of not more than 0.005 mm in any diameter. The Brinell ball is polished and free of defects. It is recommended that the ball not show a permanent change in diameter greater than 0.005 mm when pressed with the test load against the test specimens. The equipment for applying the Brinell balls and the testing using Brinell balls is conventional and can be purchased readily.

In applying the standard Brinell Hardness test the final piece of equipment necessary for the Brinell measurement system is a measuring microscope. This is a standard piece of apparatus and is generally used individually to compute the diameter of the impression in the casting. Two diameters of the impression at right angles to each other are measured and their mean value is used as the basis for calculation of the Brinell Hardness number. For routine tests and for tests to determine compliance with material or product specification, the diameter of the impression shall be read to 0.05 mm. It is often necessary to make a number of impressions on the same surface in order to get an accurate reading of hardness. As can be seen, it is necessary for a human to evaluate the diameters on a microscopic setting. The inherent inefficiencies in this operation are obvious. However, to date, these deficiencies have not been overcome on any type of a continuous system. The process of this invention has alleviated the burdens of this problem by providing a method whereby both the visual and automatic scanning of the Brinell impressions can be made to much more exacting standards.

In the process of the applicant's invention, the casting which has been impressed, is placed under a microscopic scanner television camera. This apparatus is generally described as an automatic image analysis system which produces exact quantitative information from images using equipment which combines optical, television, electronic, and computer components.

The data generated by the automatic Brinell reading apparatus is then transmitted to a computer or other electronic apparatus which can be calibrated and programmed to compute a Brinell number and generate an "accept/reject decision" regarding the specific casting. In this fashion, castings which have been placed on a conveyor can be continuously and routinely monitored for their Brinell Hardness without interjecting the normal subjective element which is necessary in most processes involving hardness measurement.

Although Brinell Hardness is but one of the many criteria which castings must meet, especially for the automotive industry, it remains one of the most important in that hardness is a general indicator for the durability and functionality of ductile iron and other cast iron castings.

While the invention has been illustrated and described in detail in the drawing and foregoing description, the same is to be considered as illustrated and not restrictive in character, it being understood that only the preferred embodiment has been shown and described and that all changes and modifications that come within the spirit of the invention and scope of the claims are also desired to be protected.

What is claimed is:

1. A process for automatically measuring the Brinell hardness of a casting for the purpose of creating data for use in making an accept/reject decision comprising the steps of:
    (a) selecting at least one surface of a casting for hardness testing and positioning said casting on retaining means such that said surface is properly aligned for surface preparation steps and the use of Brinell hardness testing apparatus;
    (b) subjecting said surface to a first surface preparation step, said first surface preparation step consisting of abrasive grinding or machining of at least a portion of the selected surface to remove irregularities in said surface;
    (c) subjecting said surface to a second surface preparation step which comprises applying a contrast enhancing material to at least a portion of said selected surface of said casting, said contrast enhancing material being selected from the group consisting of flat black paint, glass frosting, colloidal graphite, carbon black and combinations of the above;
    (d) testing the Brinell Hardness testing apparatus; and
    (e) using the Brinell Hardness data to automatically effect an accept/reject decision and computing a Brinell number, as to the suitability of said casting for its intended use.

2. A process for automatically measuring the Brinell Hardness of a casting for the purpose of creating data for use in making an accept/reject decision and computing a Brinell number comprising the steps of:
    (a) selecting at one surface of a casting for hardness testing and positioning such casting on retaining means said retaining means comprising a plurality of alignment pins mounted on a conveyor, said surface being positioned such that said surface is properly aligned for surface preparation steps and the use of Brinell Hardness testing apparatus;

(b) subjecting said surface to a first surface preparation step, said first surface preparation step consisting of abrasive grinding and/or machining of at least a portion of the selected surface to remove irregularities in said surface;

(c) subjecting said surface to a second surface preparation step which comprises applying contrast enhancing material to at least a portion of said selected surface of said casting, said surface enhancing material being selected from a group consisting of flat black paint, glass frosting, colloidal graphite, carbon black and combinations thereof;

(d) testing the Brinell Hardness of said selected surface of said casting by use of Brinell Hardness testing apparatus; and (e) using the Brinell Hardness data to automatically effect an accept/reject decision and computing a Brinell number as to the suitability of said casting for its intended use.

* * * * *